United States Patent [19]

Allander

[11] Patent Number: 4,740,206

[45] Date of Patent: Apr. 26, 1988

[54] DISPOSABLE POCKET-SIZE PACKAGE FOR EYE-RINSING LIQUID

[75] Inventor: Claes Allander, Saint Clair, France

[73] Assignee: Tobin Scandinavia AB, Alvsjo, Sweden

[21] Appl. No.: 5,166

[22] PCT Filed: Mar. 24, 1986

[86] PCT No.: PCT/SE86/00130

§ 371 Date: Nov. 13, 1986

§ 102(e) Date: Nov. 13, 1986

[87] PCT Pub. No.: WO86/05682

PCT Pub. Date: Oct. 9, 1986

[30] Foreign Application Priority Data

Mar. 27, 1985 [SE] Sweden ............................. 8501520

[51] Int. Cl.[4] ........................................ A61M 35/00

[52] U.S. Cl. .................................. 604/294; 604/297; 604/295; 604/310; 220/306; 215/309; 215/DIG. 3; 222/207

[58] Field of Search .............................. 604/294–302, 604/403, 405, 310; 220/306; 215/D3, 309; 222/108, 205, 207, 484

[56] References Cited

U.S. PATENT DOCUMENTS

| | | | |
|---|---|---|---|
| 1,692,143 | 11/1928 | Strunz | 604/301 |
| 2,626,606 | 1/1953 | Cambell | 604/301 |
| 2,847,010 | 8/1958 | Knight | 604/301 |
| 3,059,816 | 10/1962 | Goldstein | 215/309 |
| 3,910,618 | 10/1975 | Massenz | 604/294 |

*Primary Examiner*—Dalton L. Truluck
*Assistant Examiner*—Denise Whelton
*Attorney, Agent, or Firm*—Pollock, Vande Sande & Priddy

[57] ABSTRACT

A sealed, disposable pocket-size package for an eye-rinsing liquid comprises a flexible plastic bottle containing the liquid. The bottle includes a neck that is closed by a cap welded thereto. One end of the cap communicates with a connector for a liquid discharge tube that is located within the bottle, and the other end of the cap defines a liquid sprinkle member which extends into a cup-shaped eye bowl that is integral with the cap. The eye bowl is shaped to define an open mouth and includes a liquid drainage hole in a bottom wall of the bowl. The open mouth of the eye bowl is sealed closed by a cover that is tearably welded thereto, the cover including an integral plug which extends from the inner surface of the cover across the bowl into the drainage hole to also close the drainage hole.

2 Claims, 1 Drawing Sheet

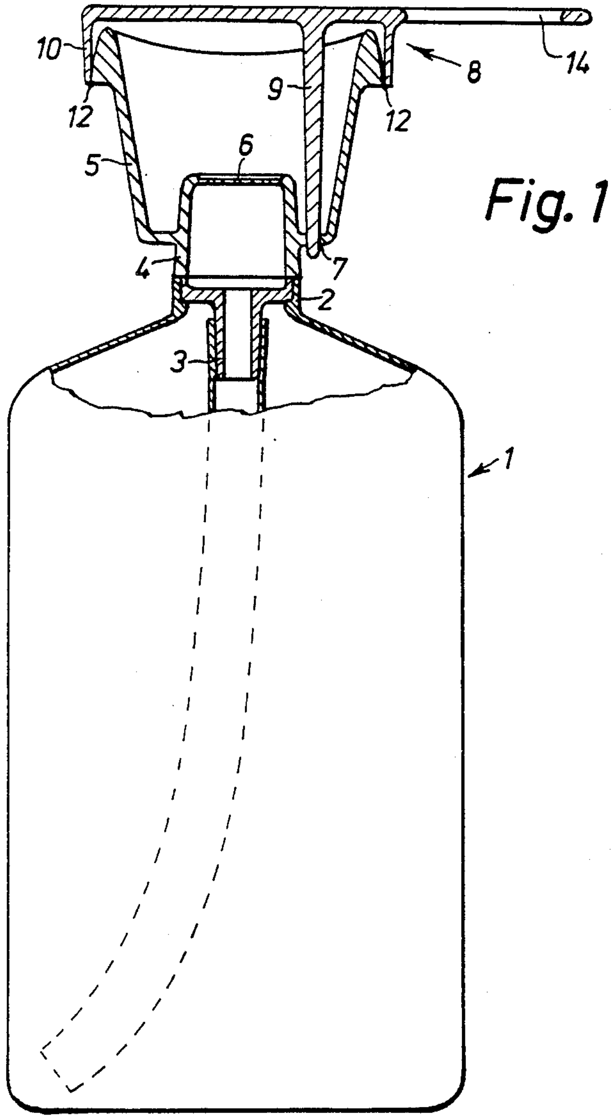
Fig. 1
Fig. 2
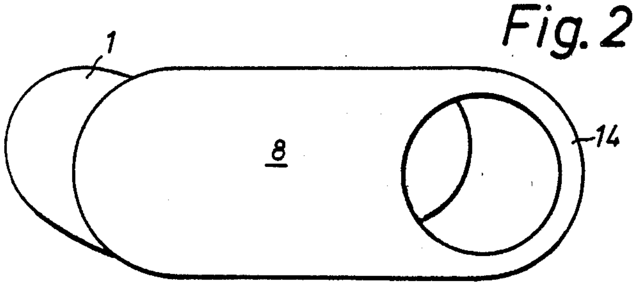

DISPOSABLE POCKET-SIZE PACKAGE FOR EYE-RINSING LIQUID

The present invention refers to a disposable pocket-size package for eye-rinsing liquids and comprising a bottle-like body preferably of flexible material and having a neck in which is mounted a connecting member for a liquid discharge tube and which is closed by a cap which is formed with a cupshaped eye-bowl and outwardly from the bottle-like body having a liquid sprinkle member, the eye-bowl having at least one opening for draining liquid from the bowl and a cover being adapted to close the mouth of said eye-bowl.

At certain working sites, particularly in industry, there is risk for the occurrence of mechanical or chemical eye injuries. Therefore, at such working sites equipments are mounted for carrying out a rinsing operation of the eyes in case of such injuries. Said equipments can either be a permanently installed eye sprinkle with water and sewage connected to the public networks or loose plastic containers which are filled with the rinsing liquid and distributed to places adjacent particularly dangerous working sites. Since every second after the occurrence of an injury is valuable before the rinsing of the eyes can be started it might even be advantageous to equip the personnel at such working sites with a rinsing liquid in a pocket package which also can be carried in a pocket of a garment such as a pair of overalls or the like.

Such pocket packages of rinsing liquid of the above-stated kind are previously known but have essential drawbacks. Firstly, the cover over the mouth of the eye-bowl is just snapped over the mouth and therefore exhibits poor sealing ability. Rinsing liquid which is forced into the bowl, particularly when the bottle-like body of flexible material such as plastic is subjected to unintentional compression, hence will leak out into the pocket of the garment. In order to provide for a drainage of used rinsing liquid the eye-bowl is furthermore provided with at least one drainage opening and this feature in combination with the-unsufficiently sealed cover makes it impossible to keep the package sterile even for a short time. For this reason the liquid in such known pocket packages has to be exchanged often and this is a supervision and maintenance work which is time-consuming as well as expensive.

The present invention therefore has for an object to eliminate the above-stated drawbacks and suggests a disposable pocket-size package of the afore-mentioned kind. The invention is essentially distinguished in that in order to provide for maintaining a long-time sterility of the filled container, (i) at least one liquid drainage hole is formed in the bottom of the eye-bowl, a closure means for said hole being supported from the inside of said cover, and (ii) the cover is provided with an axial flange closely surrounding the outer surface of said bowl and being tearably welded thereto at its free edge, the closure cap also being welded to the neck of the bottle-like body.

Owing to the invention it is now achieved that the filled package can be kept sterile for more than three years. Therefore no supervision and maintenance work on said pocket packages is required whatsoever. After a period of three years or even more it is thus sufficient to quite simply exchange all packages for new ones. Another advantage is that since the cover is welded to the outer surface of the eye-bowl and only can be destroyably torn away, the cover cannot be re-fitted and hence no re-use of the package why filling another liquid can take place, which would be reprehensible from a point of view as far as sterility is concerned. To this furthermore assists the fact that the closure cap of the bottle-like body is welded at the bottle neck so that also the latter will be broken into pieces when attempting to fill the package for re-use.

By way of example, the invention will be further described below with reference to the accompanying drawing, in which FIG. 1 is a partially sectioned side view and FIG. 2 a plan view from above of a pocket package for eye-rinsing liquid according to the invention.

The pocket package illustrated in the drawing comprises a bottle-like body 1 which preferably is made of a flexible material, particularly polypropylene. The body 1 is formed with a neck 2, in which is mounted a connecting member 3, which extends downwardly into the body 1 and on which is adapted to be mounted a liquid discharge tube (illustrated in phantom) from the bottom of the body 1. Furthermore, the neck 2 is closed by a small cup-shaped cap 4 from the outer surface of which extends a large cup-like eye bowl 5. The end of the cap 4 remote from the bottle-like body 1 also carries a liquid sprinkle member 6 for the rinsing liquid which is to be accommodated in the body 1. The bottom wall of eye-bowl 5 adjacent to and outward wall of is formed with at least one opening 7 for draining rinsing liquid from the bowl, and at its free mouth the bowl 5 is closed by a cover 8. As evident from FIG. 2 the body 1 preferably can be slightly curved in the transverse direction for adaptation to the body contour of the wearer such as is known per se.

In order to obtain the object of the invention, namely to provide for the maintenance of a long-term sterility of the package since the same has been filled initially with rinsing liquid which can be constituted of a sodium chloride solution, the liquid drainage hole 7 is formed in the bottom of the eye-bowl 5. In order to close said hole 7 a closure means or plug 9 is supported from the inside of the cover 8 so that no bacteria or pollutions can penetrate into the eye-bowl 5 and hence the liquid-filled body 1.

As known per se, the cover 8 is formed with an axial flange 10 which grips over the outer surface of the bowl 5 adjacing the mouth thereof, where the bowl for the rest can be made with a form-stiffening rib which is indicated in the drawing. In order to provide for the maintenance of the sterility of the filled package during very long time, such as three years or more, the cover 8 is welded tearably by a weld 12 to the free edge of the flange 10 around the whole eye-bowl 5. Thereby is secured firstly a sealed closure of the package 1 but at the same time also that the package cannot be re-used since the cover 8 after tearing away and emptying of the liquid from the bottle-like body 1 cannot be rigidly re-secured to the bowl 5.

Usually bottle-like packages of the present kind are provided with external threads on the neck 2 for cooperation with the internal threads in the cap 4 and so can also be the case in the present inventive subject matter. In order to further prevent the possibilities of a non-desired re-use of the package after re-filling of rinsing liquid under non-sterile conditions it is preferable, however, that the cap 4 be welded to the neck 2. Attempts to remove the cap 4 then only will cause the whole package to be broken into pieces. Moreover, it is to be noted that the connection member 3 has been illustrated in the drawing as a separate insert piece which is seated on shoulders provided on the inner surface of the neck 2, and which is kept located by the mounting of the cap 4. Many other designs of this connecting member 3 are also possible, however, such as forming it integrally with the cap 4. In order to facilitate the tearing away of the cover 8 this might suitably be formed with a laterally protruding finger-grip ring 14.

I claim:

1. A sealed, disposable pocket-size package for an eye-rinsing liquid comprising a flexible plastic bottle for containing the liquid, said bottle including a liquid discharge tube extending into said bottle said bottle defining a neck portion that is closed by a plastic cap welded thereto, said cap having one end closely adjacent to said neck portion in communication with said liquid discharge tube, said cap having side walls extending from said one end thereof away from said bottle to a second end of said cap which defines liquid sprinkle means, said cap providing fluid communication between said liquid discharge tube and said sprinkle means a cupshaped eye bowl integral with said cap, said eye bowl including a bottom wall integral with and extending outwardly of the side walls of said cap between said first and second ends of said cap, said eye bowl also including outwardly divergent side walls extending from said bottom wall away from said neck portion of said bottle in surrounding relation to and beyond said sprinkle means to define an enlarged mouth of said eye bowl at a location remote from said bottle, said bottom wall of said bowl having a liquid discharge opening therein adjacent to and outward of the side walls of said cap, and a detachable plastic closure structure for sealingly closing said mouth and said liquid drainage opening of said eye bowl, said closure structure including a cover portion which overlies the mouth of said eye bowl and which has a flange that extends around and is tearably welded to and about the exterior edges of said mouth, said cover portion including an integral plug member which extends from a position adjacent said mouth of said eye bowl through the interior of said eye bowl to the bottom wall of said eye bowl and into said liquid drainage opening.

2. The package of claim 1 wherein said closure structure includes a finger-grip ring portion extending outwardly of said cover portion for use in tearing said closure structure off of said eye bowl.

* * * * *